(12) United States Patent
Friede et al.

(10) Patent No.: US 6,558,670 B1
(45) Date of Patent: May 6, 2003

(54) VACCINE ADJUVANTS

(75) Inventors: Martin Friede, Court St Etienne (BE); Philippe Hermand, Court St Etienne (BE)

(73) Assignee: SmithKline Beechman Biologicals s.a., Rixensart (BE)

( * ) Notice: Subject to any disclaimer, the term of this patent is extended or adjusted under 35 U.S.C. 154(b) by 0 days.

(21) Appl. No.: 09/301,829

(22) Filed: Apr. 29, 1999

(30) Foreign Application Priority Data

Apr. 19, 1999 (BE) .............................................. 9908885

(51) Int. Cl.$^7$ ............................................... A61K 39/39

(52) U.S. Cl. ............................... 424/184.1; 424/278.1; 424/283.1; 514/25

(58) Field of Search ........................... 424/184.1, 278.1, 424/283.1; 514/25

(56) References Cited

U.S. PATENT DOCUMENTS

| | | | |
|---|---|---|---|
| 5,057,540 A | 10/1991 | Kensil et al. | |
| 6,231,859 B1 * | 5/2001 | Kensil | ...................... 424/184.1 |
| 6,406,705 B1 | 6/2002 | Davis et al. | ............. 424/278.1 |

FOREIGN PATENT DOCUMENTS

| | | |
|---|---|---|
| EP | 0 109 942 B1 | 3/1991 |
| EP | 0 468 520 | 7/1991 |
| EP | 0 362 279 | 1/1995 |
| EP | 0 671 948 | 8/1997 |
| EP | 0 689 454 | 9/1997 |
| EP | 0 855 184 | 7/1998 |
| GB | 2 122 204 A | 1/1984 |
| WO | WO95/17210 | 6/1995 |
| WO | WO96/02555 | 2/1996 |
| WO | WO96/11711 | 4/1996 |
| WO | WO96/33739 | 10/1996 |
| WO | WO98/15287 | 4/1998 |
| WO | WO98/16247 | 4/1998 |
| WO | WO 98/18810 | 5/1998 |
| WO | WO98/20734 | 5/1998 |
| WO | WO98/28037 | 7/1998 |
| WO | WO 98/37919 | 9/1998 |
| WO | WO 98/40100 | 9/1998 |
| WO | WO 98/55495 | 12/1998 |
| WO | WO 98/55609 | 12/1998 |
| WO | WO98/56414 | 12/1998 |
| WO | WO98/56415 | 12/1998 |
| WO | WO99/10008 | 3/1999 |
| WO | WO 99/12565 | 3/1999 |
| WO | WO 99/33488 | 7/1999 |
| WO | WO 99/61056 | 12/1999 |
| WO | WO 99/62923 | 12/1999 |
| WO | WO 00/09159 | 2/2000 |

OTHER PUBLICATIONS

Mowat et al., "Immune–stimulating complexes containing !uil A and protein antigen prime class etc.", *Immunology*, 72, pp. 317–322 (1991).

Kensil et al., "Synergistic Action of QS–21 and CpG Adjuvants", *X5 DNA Vaccines*, Abstract No. 218, (1999).

O. Gisvold, "Digitonin and Phytosterol From the See of Digitalis Purpurea", *Phytochemical Notes*, 23(7), pp. 664–665 (1933).

Yoshikawa et al., "Bioactive Saponins and Glycosides, III. Horse Chestnur (1): etc.", *Chem. Phar. Bull.*, 44(8), pp. 1454–1463 (1996).

Estrada et al., "Adjuvanta ction of *Chenopodium quinoa* saponins on the induction etc.", *Com. Immun. Microbiol. & Infect Dis.*, 21, pp. 225–236 (1998).

Kensil, "Saponins as Vaccine Adjuvants", *Critical Reviews in Therapeutic Drug Carrier Systems*, 13(1&2), pp. 1–55 (1996).

Lacaille–Dubois et al., "A review of the biological and pharmacological activities of saponins", *Phytomedicine*, 2(4), pp. 363–386 (1996).

Gizurarson et al., "Pharmaceutical Excipients and Absorpotion Promoters as Immunostimulatns etc.", *Vacgine Research*, 3(1), pp. 23–29 (1994).

Bomford et al., "Adjuvanticity and ISCOM formation by structually diverse saponins", *Vaccine*, 10(9), pp. 572–577 (1992).

Krieg et al., "CpG motifs in bacterial DNA trigger direct B–cell activation", *Nature*, 374, pp. 546–549 (1995).

Kensil et al., "Separation and Characterization of Saponins with adjuvant Activty etc.", *Journal of Immunology*, 146(2), pp. 431–437 (1991).

Chavali et al., "Adjuvant Effects of Orally Administered Saponins on Humoral etc.", *Immunobiol.*, 174, pp. 347–359 (1987).

Sasaki et al., "Induction of Systemic and Mucosal Immune Responses to Human etc.", *Journal of Virology*, 72(6), pp. 4931–4939 (1998).

Majarak et al., "Immune responses of mice to inactivated rabies vaccine etc.", *Can. J. Microbiol.*, 32, pp. 414–420 (1986).

Mowat et al., "ISCOMS—a novel strategy for mucosal immunization?", Immunology Today, 12(11), pp. 383–385 (1991).

Brazolot–Millan et al., "CpG DNA can induce strong Th1 humoral and cell–mediated immune etc.", *Proc. Natl. Acad. Sci. USA*, 95, pp. 15553–15558 (1988).

(List continued on next page.)

*Primary Examiner*—Laurie Scheiner
(74) *Attorney, Agent, or Firm*—Jeffrey A. Sutton; Stephen Venetianer; Charles M. Kinzig

(57) ABSTRACT

The present invention relates to adjuvant compositions which are suitable to be used in vaccines. In particular, the adjuvant compositions of the present invention comprises a saponin and an immunostimulatory oligonucleotide, preferably the saponins used in said adjuvant combinations are haemolytic. Also provided by the present invention are vaccines comprising the adjuvants of the present invention and an antigen. Further provided are methods of manufacture of the adjuvants and vaccines of the present invention and their use as medicaments.

5 Claims, 1 Drawing Sheet

OTHER PUBLICATIONS

McCluskie et al., "Cutting Edge:CpG DNA is a potent enhancer of systemic and mucosal etc.", *J. Immunol.*, 161(9), pp. 4463–4466 (1998).

Davis et al., "CpG DNA is a patent enhancer of specific immunity in mice etc.", *J. Immunol.*, 160(2), pp.870–876 (1998).

Dennis M. Klinman, "Therapeutic Applications of CpG–Containing Oligodeoxynucleotides", *Antisense & Nucleic Acid Drug Development*, 8: 181–184 (1998).

Liu, et al., "Immunostimulatory CpG Oligodeoxynucleotides Enhance the Immune Response to Vaccine Strategies Involving Granulocyte–Macrophage Colony–Stimulating Factor", *Blood*, 92(10): 3730–3736 (1998).

Krieg, et al., "The Role of CpG Dinucleotides in DNA Vaccines", *Trends in Microbiology*, 6(1): 23–27 (1998).

So, et al., "Effect of a novel Saponin Adjuvant Derived from *Quillaja saponaria* on the Immune Response to Recombinant Hepatitis B Surface Antigen", *Mol. Cells*, 7(2) : 178–186 (1997).

Lipford, et al., "CpG–Containing Synthetic Oligonucleotides Promote B and Cytotoxic T Cell Responses to Protein Antigen: A New Class of Vaccine Adjuvants", *Eur. J. Immunology*, 27: 2340–2344 (1997).

Moldoveanu, et al., "CpG DNA, A Novel Immune Enhancer for Systemic and Mucosal Immunization with Influenza Virus", *Vaccine*, 16: 1216–1224 (1998).

Klinman, et al., "CpG Motifs as Immune Adjuvants", *Vaccine*, 17: 19–25 (1999).

\* cited by examiner

Figure 1: serum IgG to lipo-OspA in mice
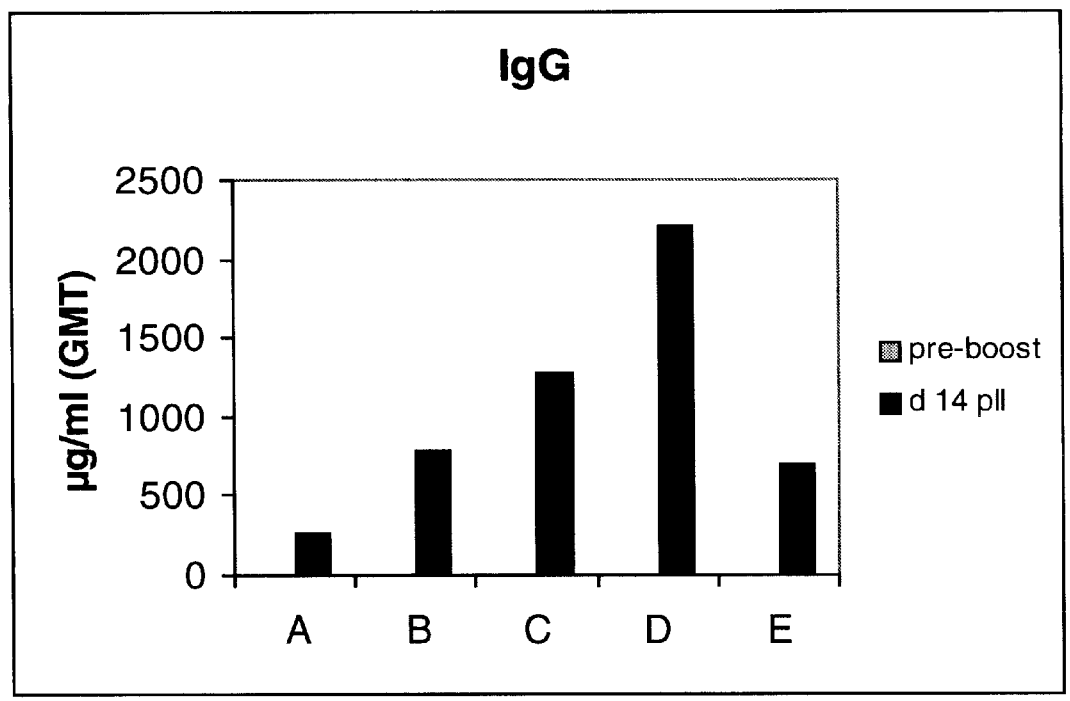
Figure 2: LA2 titres in mice
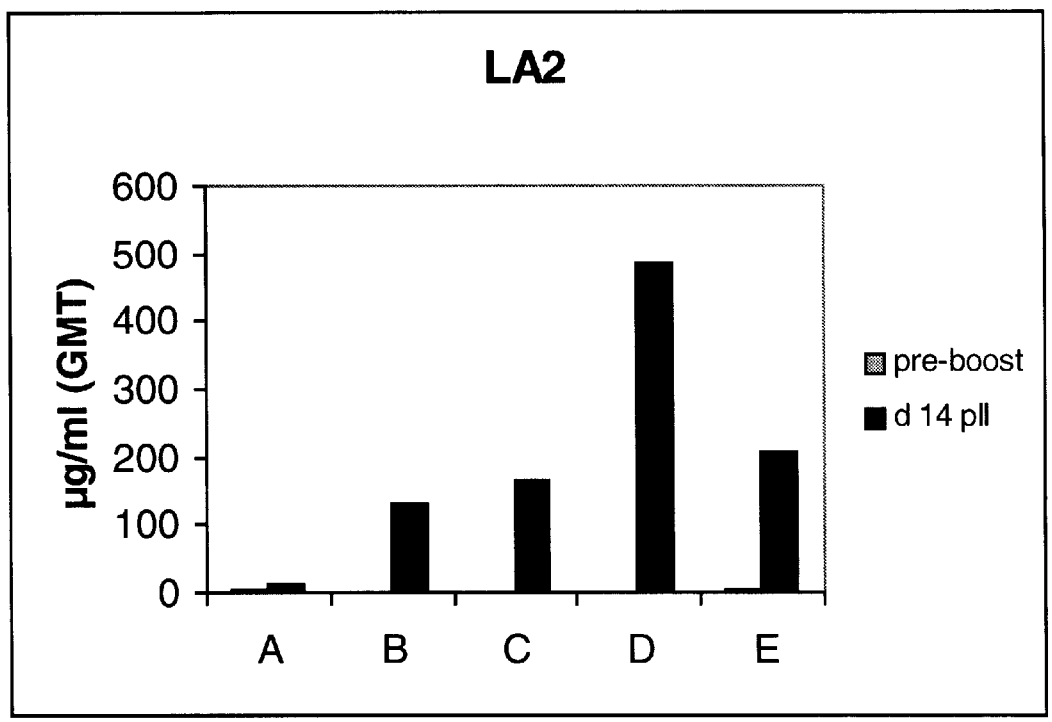

VACCINE ADJUVANTS

The present invention relates to adjuvant compositions which are suitable to be used in vaccines. In particular, the adjuvant compositions of the present invention comprises a saponin and an immunostimulatory oligonucleotide, preferably the saponins used in said adjuvant combinations are haemolytic. Also provided by the present invention are vaccines comprising the adjuvants of the present invention and an antigen. Further provided are methods of manufacture of the adjuvants and vaccines of the present invention and their use as medicaments.

BACKGROUND OF THE INVENTION

Immunostimulatory oligonucleotides containing unmethylated CpG dinucleotides ("CpG") and are known in the art as being adjuvants when administered by both systemic and mucosal routes (WO 96/02555, EP 468520, Davis et al., J.Immunol, 1998, 160(2):870–876; McCluskie and Davis, J.Immunol., 1998, 161(9):4463–6). CpG is an abbreviation for cytosine-guanosine dinucleotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequence containing oligonucleotides can activate various immune subsets, including natural killer cells (which produce interferon γ and have cytolytic activity) and macrophages (Wooldrige et al Vol. 89 (no. 8), 1977). Although other unmethylated CpG containing sequences not having this consensus sequence have now been shown to be immunomodulatory.

CpG when formulated into vaccines, is generally administered in free solution together with free antigen (WO 96/02555; McCluskie and Davis, supra) or covalently conjugated to an antigen (PCT Publication No. WO 98/16247), or formulated with a carrier such as aluminium hydroxide ((Hepatitis surface antigen) Davis et al. supra ; Brazolot-Millan et al., Proc.Natl.Acad.Sci., USA, 1998, 95(26), 15553–8).

Saponins are taught in: Lacaille-Dubois, M and Wagner H. (1996. A review of the biological and pharmacological activities of saponins. Phytomedicine vol 2 pp 363–386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit Rev Ther Drug Carrier Syst, 1996, 12 (1–2):1–55; and EP0 362 279B1.

Particulate structures, termed Immune Stimulating Complexes (ISCOMS), comprising fractions of Quil A are haemolytic and have been used in the manufacture of vaccines (Morein, B., EP 0 109 942 B 1). These structures have been reported to have adjuvant activity (EP 0 109 942 B1; WO 96/11711).

The haemolytic saponins QS21 and QS 17 (HPLC purified fractions of Quil A) have been described as potent systemic adjuvants, and the method of their production is disclosed in U.S. Pat. No. 5,057,540 and EP 0 362 279 B 1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431–437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Other saponins which have been used in systemic vaccination studies include those derived from other plant species such as Gypsophila and Saponaria (Bomford et al., Vaccine, 10(9):572–577, 1992).

Saponins are also known to have been used in mucosally applied vaccine studies, which have met with variable success in the induction of immune responses. Quil-A saponin has previously been shown to have no effect on the induction of an immune response when antigen is administered intranasally (Gizurarson et al. 1994. Vaccine Research 3, 23–29). Whilst, other authors have used this adjuvant with success (Maharaj et al., Can.J.Microbiol, 1986, 32(5):414–20; Chavali and Campbell, Immunobiology, 174(3):347–59). ISCOMs comprising Quil A saponin have been used in intragastric and intranasal vaccine formulations and exhibited adjuvant activity (McI Mowat et al., 1991, Immunology, 72, 317–322; McI Mowat and Donachie, Immunology Today, 12, 383–385).

QS21, the non-toxic fraction of Quil A, has also been described as an oral or intranasal adjuvant (Sumino et al., J.Virol., 1998, 72(6):4931–9; WO 98/56415).

The use of other saponins in intranasal vaccination studies has been described. For example, Chenopodium quinoa saponins has been used in both intranasal and intragastric vaccines (Estrada et al., Comp. Immunol. Microbiol. Infect. Dis., 1998, 21(3):225–36).

BRIEF SUMMARY OF THE INVENTION

The present invention provides an adjuvant composition comprising a saponin and an immunostimulatory oligonucleotide; particularly wherein said saponin has haemolytic activity. Preferred saponins include Quil A, QS21, QS7, QS 17, β-escin, or digitonin. Preferred immunostimulatory oligonucleotides comprise the following sequence: Purine, Purine, C, G, pyrimidine, pyrimidine.

The present invention also provides preferred vaccine compositions containing the claimed adjuvant compositions;

methods of treatment by administration of vaccines containing the claimed adjuvant compositions; and methods of inducing a systemic antigen-specific immune response comprising administration of vaccine compositions comprising a haemolytic saponin and a Cp G molecule.

BRIEF DESCRIPTION OF THE DRAWINGS

FIG. 1 represents the OspA-specific titer of serum IgG, 14 days after nasal boosting using A:PBS; B: 20 μg CpG 1001 (TCC ATG AGC TTC CTG ACG TT, Krieg 1826); C: 5 μg QS21 (obtained from Cambridge Biotech, USA); D: 20 μg CpG 1001+5 μg QS21; or, E: by intra muscular injection of 1 μg lipo-OspA adsorbed onto alum (50 μg).

FIG. 2 represents the OspA-specific LA2 titer in the mouse sera, 14 days after nasal boosting using A:PBS; B: 20 μg CpG 1001 (TCC ATG AGC TTC CTG ACG TT, Krieg 1826); C: 5 μg QS21 (obtained from Cambridge Biotech, USA); D: 20 μg CpG 1001+5 μg QS21; or, E: by intra muscular injection of 1 μg lipo-OspA adsorbed onto alum (50 μg).

DETAILED DESCRIPTION OF THE INVENTION

The present invention relates to the surprising finding that immuno-stimulatory oligonucleotides (CpG) and saponin combinations are extremely potent adjuvants. Accordingly, there is provided an adjuvant composition comprising a saponin and an immunostimulatory oligonucleotide. In a preferred form of the present invention the saponin and oligonucleotides in the adjuvant and vaccine compositions act synergistically in the induction of antigen specific antibody.

The adjuvant combinations of the present invention are used in the formulation of vaccines, which vaccines may be administered via the systemic or mucosal route. Preferably, when the vaccines are used for mucosal administration the adjuvant combination comprises a haemolytic saponin.

The preferred oligonucleotides for use in adjuvants or vaccines of the present invention preferably contain two or more CpG motifs separated by six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. No. 5,666,153, U.S. Pat. No. 5,278,302 and WO95/26204.

Preferred oligonucleotides have the following sequences: The sequences preferably contain all phosphorothioate modified internucleotide linkages.

OLIGO 1: TCC ATG ACG TTC CTG ACG TT (SEQ ID NO:1)

OLIGO 2: TCT CCC AGC GTG CGC CAT (SEQ ID NO:2)

OLIGO 3: ACC GAT GAC GTC GCC GGT GAC GGC ACC ACG (SEQ ID NO:3)

The CpG oligonucleotides utilised in the present invention may be synthesized by any method known in the art (eg EP 468520). Conveniently, such oligonucleotides may be synthesized utilising an automated synthesizer.

The oligonucleotides utilised in the present invention are typically deoxynucleotides. In a preferred embodiment the internucleotide bond in the oligonucleotide is phosphorodithioate, or more preferably phosphorothioate bond, although phosphodiesters are within the scope of the present invention. Oligonucleotide comprising different internucleotide linkages are contemplated, e.g. mixed phosphorothioate phophodiesters. Other internucleotide bonds which stabilise the oligonucleotide may be used.

The saponins which may be used in the adjuvant combinations of the present invention include those derived from the bark of Quillaja Saponaria Molina, termed Quil A, and fractions thereof, described in U.S. Pat. No. 5,057,540 and "Saponins as vaccine adjuvants", Kensil, C. R., *Crit Rev Ther Drug Carrier Syst*, 1996, 12 (1–2):1–55; and EP 0 362 279 B1. Particularly preferred fractions of Quil A are QS21, QS7, and QS17.

β-Escin is another preferred haemolytic saponins for use in the adjuvant compositions of the present invention. Escin is described in the Merck index ($12^{th}$ ed: entry 3737) as a mixture of saponins occurring in the seed of the horse chestnut tree, Lat: *Aesculus hippocastanum*. Its isolation is described by chromatography and purification (Fiedler, *Arzneimittel*-Forsch. 4, 213 (1953)), and by ion-exchange resins (Erbring et al., U.S. Pat. No. 3,238,190). Fractions of escin, α and β, have been purified and shown to be biologically active (Yoshikawa M, et al. (*Chem Pharm Bull* (Tokyo) 1996 Aug;44(8):1454–1464)). β-escin is also known as aescin.

Another preferred haemolytic saponin for use in the present invention is Digitonin. Digitonin is described in the Merck index ($12^{th}$ Edition, entry 3204) as a saponin, being derived from the seeds of *Digitalis purpurea* and purified according to the procedure described Gisvold et al., *J.Am.Pharm.Assoc.*, 1934, 23, 664; and Ruhenstroth-Bauer, *Physiol.Chem.*, 1955, 301, 621. Its use is described as being a clinical reagent for cholesterol determination.

The adjuvant combinations of the present invention, represent a class of mucosal adjuvants suitable for application in humans to replace systemic vaccination by mucosal vaccination. In a preferred form of the present invention pure saponins such as Quil A, or derivatives thereof, including QS21; Escin; Digitonin; or Gypsophila or *Chenopodium quinoa* saponins in combination with immunostimulatory oligonucleotides may be used as adjuvants for the mucosal administration of antigens to achieve a systemic immune response.

In an alternative aspect of the present invention there is provided a mucosal adjuvant, suitable for vaccines to be administered to a mucosal surface. For mucosal administration preferably the composition of the invention comprise a haemolytic saponin. Haemolytic saponin, or saponin preparation, within the meaning of this invention is to be determined with reference to the following assay.

1. Fresh blood from guinea pigs is washed with phosphate buffered saline (PBS) 3 times in a desk-top centrifuge. After resuspension to the original volume the blood is further diluted 10 fold in PBS.
2. 50 μl of this blood suspension is added to 800 μl of PBS containing two-fold dilutions of surfactant or saponin.
3. After 8 hours the haemolysis is assessed visually or by measuring the optical density of the supernatant. The presence of a red supernatant, which absorbs light at 570 nm indicates the presence of haemolysis.
4. The results are expressed as the concentration of the first saponin dilution at which hemolysis no longer occurs.

For the purposes of this invention the saponin adjuvant preparation is haemolytic if it lyses the erythrocytes at a concentration of less than 0.1%. As means of reference, substantially pure samples of QuilA, QS21, QS7, Digitonin, and β-escin are all haemolytic saponins as defined in this assay.

The saponins of the present invention may be in the form of an aqueous solution of saponin or in the form of aggregates such as micelles, or ordered aggregates in combination with other non-saponin constituents. For example, the saponin may be in the form of an ISCOM or a liposome in the presence of additional cholesterol and phospholipid. Alternatively the saponin may be associated with a particulate carrier such as chitosan. The saponin may also be in a dry state such as a powder. The final formulations in the form as they are administered to the mucosal surface of the vaccine are preferably haemolytic in nature.

Preparations of more than one saponin in the adjuvant combinations of the present invention are also form part of the present invention. For example combinations of at least two of the following group comprising QS21, QS7, Quil A, β-escin, or digitonin. Additionally, the compositions of the present invention may comprise combinations of more than one immunostimulatory oligonucleotide.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, . . . ), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, Vaccine, 1992, 10, 915–920) or purified or recombinant proteins thereof, such as HA, NP, NA, or M proteins, or combinations thereof), or derived from bacterial pathogens such as Neisseria spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi*; Moraxella spp, including *M catarrhalis*, also known as *Branhamella catarrhalis* (for example high and low molecular weight adhesins and invasins); Bordetella spp, including *B. pertussis* (for example pertactin, pertussis toxin or derivatives thereof, filamenteous hemagglutinin, adenylate cyclase, fimbriae), *B. parapertussis* and *B. bronchiseptica*; Mycobacterium spp., including *M. tuberculosis* (for example ESAT6, Antigen 85A, -B or -C), *M. bovis, M. leprae, M. avium, M. paratuberculosis, M. smegmatis*; Legionella spp, including *L. pneumophila*; Escherichia spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); Vibrio spp, including *V cholera* (for example cholera toxin or derivatives thereof); Shigella spp, including *S. sonnei, S. dysenteriae, S. flexnerii*; Yersinia spp, including *Y enterocolitica* (for example a Yop protein), *Y pestis, Y. pseudotuberculosis*; Campylobacter spp, including *C. jejuni* (for example toxins, adhesins and invasins) and C. coli; Salmonella spp, including *S. typhi, S. paratyphi, S. choleraesuis, S. enteritidis*; Listeria spp., including *L. monocytogenes*; Helicobacter spp, including *H. pylori* (for example urease, catalase, vacuolating toxin); Pseudomonas spp, including *P. aeruginosa*; Staphylococcus spp., including *S. aureus, S. epidermidis*; Enterococcus spp., including *E. faecalis, E. faecium*; Clostridium spp., including *C. tetani* (for example tetanus toxin and derivative thereof), *C. botulinum* (for example botulinum toxin and derivative thereof), *C. difficile* (for example clostridium toxins A or B and derivatives thereof); Bacillus spp., including *B. anthracis* (for example botulinum toxin and derivatives thereof); Corynebacterium spp., including *C. diphtheriae* (for example diphtheria toxin and derivatives thereof); Borrelia spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii*; Ehrlichia spp., including *E. equi* and the agent of the Human Granulocytic Ehrlichiosis; Rickettsia spp, including *R. rickettsii*; Chlamydia spp., including *C. trachomatis* (for example MOMP, heparin-binding proteins), *C. pneumoniae* (for example MOMP, heparin-binding proteins), *C. psittaci*; Leptospira spp., including *L. interrogans*; Treponema spp., including *T. pallidum* (for example the rare outer membrane proteins), *T denticola, T. hyodysenteriae*; or derived from parasites such as Plasmodium spp., including *P. falciparum*; Toxoplasma spp., including *T. gondii* (for example SAG2, SAG3, Tg34); Entamoeba spp., including *E. histolytica*; Babesia spp., including *B. microti*; Trypanosoma spp., including *T cruzi*; Giardia spp., including *G. lamblia*; Leshmania spp., including *L. major*; Pneumocystis spp., including *P. carinii*; Trichomonas spp., including *T. vaginalis*; Schisostoma spp., including *S. mansoni*, or derived from yeast such as Candida spp., including *C. albicans*; Cryptococcus spp., including *C. neoformans*.

Preferred bacterial vaccines comprise antigens derived from Streptococcus spp, including *S. pneumoniae* (for example capsular polysaccharides and conjugates thereof, PsaA, PspA, streptolysin, choline-binding proteins)and the protein antigen Pneumolysin (Biochem Biophys Acta, 1989, 67, 1007; Rubins et al., Microbial Pathogenesis, 25, 337–342), and mutant detoxified derivatives thereof (WO 90/06951; WO 99/03884). Other preferred bacterial vaccines comprise antigens derived from Haemophilus spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Derivatives of Hepatitis B Surface antigen are well known in the art and include, inter alia, those PreS1, PreS2 S antigens set forth described in European Patent applications EP-A-414 374; EP-A-0304 578, and EP 198–474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papilloma Virus (HPV) considered to be responsible for genital warts, (HPV 6 or HPV 11 and others), and the HPV viruses responsible for cervical cancer (HPV16, HPV18 and others).

Particularly preferred forms of genital wart prophylactic, or therapeutic, vaccine comprise L1 particles or capsomers, and fusion proteins comprising one or more antigens selected from the HPV 6 and HPV 11 proteins E6, E7, L1, and L2.

The most preferred forms of fusion protein are: L2E7 as disclosed in WO 96/26277, and proteinD(1/3)-E7 disclosed in GB 9717953.5 (PCT/EP98/05285).

A preferred HPV cervical infection or cancer, prophylaxis or therapeutic vaccine, composition may comprise HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably E5 for example; particularly preferred embodiments of this includes a VLP comprising L1E7 fusion proteins (WO 96/11272).

Particularly preferred HPV 16 antigens comprise the early proteins E6 or E7 in fusion with a protein D carrier to form Protein D- E6 or E7 fusions from HPV 16, or combinations thereof; or combinations of E6 or E7 with L2 (WO 96/26277).

Alternatively the HPV 16 or 18 early proteins E6 and E7, may be presented in a single molecule, preferably a Protein D-E6/E7 fusion. Such vaccine may optionally contain either or both E6 and E7 proteins from HPV 18, preferably in the form of a Protein D-E6 or Protein D-E7 fusion protein or Protein D E6/E7 fusion protein.

The vaccine of the present invention may additionally comprise antigens from other HPV strains, preferably from strains HPV 31 or 33.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P.falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in Plasmodium spp.

The formulations may also contain an anti-tumour antigen and be useful for the immunotherapeutic treatment cancers.

For example, the adjuvant formulation finds utility with tumour rejection antigens such as those for prostrate, breast, colorectal, lung, pancreatic, renal or melanoma cancers. Exemplary antigens include MAGE 1 and MAGE 3 or other MAGE antigens for the treatment of melanoma, PRAME, BAGE or GAGE (Robbins and Kawakami, 1996, Current Opinions in Immunology 8, pps 628–636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma. Other Tumor-Specific antigens are suitable for use with adjuvant of the present invention and include, but are not restricted to Prostate specific antigen (PSA) or Her-2/neu, KSA (GA733), MUC-1 and carcinoembryonic antigen (CEA). Accordingly in one aspect of the present invention there is provided a vaccine comprising an adjuvant composition according to the invention and a tumour rejection antigen.

Additionally said antigen may be a self peptide hormone such as whole length Gonadotrophin hormone releasing hormone (GnRH, WO 95/20600), a short 10 amino acid long peptide, in the treatment of many cancers, or in immunocastration.

It is foreseen that compositions of the present invention will be used to formulate vaccines containing antigens derived from Borrelia sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (E.Coli) termed (Lipo-OspA) or a non-lipidated derivative. Such non-lipidated derivatives include the non-lipidated NS1-OspA fusion protein which has the first 81 N-terminal amino acids of the non-structural protein (NS 1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1) and allergen non-specific antigens (for example peptides derived from human IgE, including but not restricted to the stanworth decapeptide (EP 0 477 231 B 1)).

The vaccine preparations of the present invention may be used to protect or treat a mammal susceptible to, or suffering from disease, by means of administering said vaccine via a systemic route, such as intramuscular, or subcutaneous administration; or by a mucosal route, such as the oral/alimentary or nasal route. Alternative mucosal routes are intravaginal and intra-rectal. The preferred route of administration is via the nasal route, termed intranasal vaccination. Methods of intranasal vaccination are well known in the art, including the administration of a droplet, spray, or dry powdered form of the vaccine into the nasopharynx of the individual to be immunised. Nebulised or aerosolised vaccine formulations also form part of this invention. Enteric formulations such as gastro resistant capsules and granules for oral administration, suppositories for rectal or vaginal administration also form part of this invention. The present invention may also be used to enhance the immunogenicity of antigens applied to the skin (transdermal or transcutaneous delivery WO 98/20734 ; WO 98/28037).

The amount of protein in each vaccine dose is selected as an amount which induces an immunoprotective response without significant, adverse side effects in typical vaccinees.

Such amount will vary depending upon which specific immunogen is employed and how it is presented. Generally, it is expected that each dose will comprise 1–1000 μg of protein, preferably 1–500 μg, preferably 1–100 μg, most preferably 1 to 50 μg. An optimal amount for a particular vaccine can be ascertained by standard studies involving observation of appropriate immune responses in vaccinated subjects. Following an initial vaccination, subjects may receive one or several booster immunisation adequately spaced. Such a vaccine formulation may be applied to a mucosal surface of a mammal in either a priming or boosting vaccination regime; or alternatively be administered systemically, for example via the transdermal, subcutaneous or intramuscular routes.

The amount of CpG or immunostimulatory oligonucleotides in the adjuvants or vaccines of the present invention is generally small, but depending on the vaccine formulation may be in the region of 1–1000 μg per dose, preferably 1–500μg per dose, and more preferably between 1 to 100 μg per dose.

The amount of saponin for use in the adjuvants of the present invention may be in the region of 1–1000 μg per dose, preferably 1–500 μg per dose, more preferably 1–25 μg per dose, and most preferably between 1 to 100 μg per dose. The ratio of CpG:saponin (w/w) will, therefore, be in the range of 1:1000 to 1000:1, and will typically be in the range of 1:100 to 100:1, and preferably in the range of 1:10 to 10:1.

The CpG used in the adjuvant combinations of the present invention may be in free solution of may be complexed to particulate carriers, for example aluminium or calcium salts, liposomes, ISCOMs, oil in water emulsions, polylactide polyglycolide microparticles, or alginates. Preferably said carriers are cationic. The vaccines of the present invention further comprise an antigen which may be associated with the CpG-carrier complex, or may not be associated with the CpG-carrier complex. In this case, the antigen may be free suspension or associated with a separate carrier.

The CpG and saponin in the adjuvants or vaccines of the present invention may be separate or associated. For example, the CpG and saponin may be in free suspension or may be associated via a carrier such as aluminium hydroxide or by a cationic liposome or ISCOM.

The saponins forming part of the present invention may be separate in the form of micelles, or may be in the form of large ordered structures such as ISCOMs (EP 0 109 942 B1) or liposomes (WO 96/33739) when formulated with cholesterol and lipid, or in the form of an oil in water emulsion (WO 95/17210). The saponins may preferably be associated with a metallic salt, such as aluminium hydroxide or aluminium phosphate (WO 98/15287).

In a similar embodiment of the present invention the haemolytic saponin preparations will further be combined with other adjuvants including Monophosphoryl Lipid A and its non-toxic derivative 3-de-O-acylated monophosphoryl lipid A. Alternatively the saponin formulations may be combined with vaccine vehicles composed of chitosan or other polycationic polymers, polylactide and polylactide-coglycolide particles, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

3 De-O-acylated monophosphoryl lipid A is a well known adjuvant manufactured by Ribi Immunochem, Montana. It can be prepared by the methods taught in GB 2122204B. A preferred form of 3 De-O-acylated monophosphoryl lipid A is in the form of an emulsion having a small particle size less than 0.2 μm in diameter (EP 0 689 454 B1). Particularly preferred adjuvants are combinations of 3D-MPL and QS21 (EP 0 671 948 B1), oil in water emulsions comprising 3D-MPL and QS21 (WO 95/17210, WO 98/56414), or 3D-MPL formulated with other carriers (EP 0 689 454 B1).

The saponin may or may not be associated physically with the antigen either through direct linkage or by co-interaction with the same particulate carrier molecule (GB9822712.7; WO 98/16247)

The vaccines of the present invention may also be administered via the oral route. In such cases the pharmaceutically acceptable excipient may also include alkaline buffers, or enteric capsules or microgranules. The vaccines of the present invention may also be administered by the vaginal route. In such cases, the pharmaceutically acceptable excipients may also include emulsifiers, polymers such as CARBOPOL®, and other known stablilisers of vaginal creams and suppositories. The vaccines of the present invention may also be administered by the rectal route. In such cases the excipients may also include waxes and polymers known in the art for forming rectal suppositories.

The formulations of the present invention maybe used for both prophylactic and therapeutic purposes. Accordingly, the present invention provides for a method of treating a mammal susceptible to or suffering from an infectious disease or cancer, or allergy, or autoimmune disease. In a further aspect of the present invention there is provided a vaccine or adjuvant combination, comprising a saponin and CpG, as herein described for use as a medicament. Vaccine preparation is generally described in New Trends and Developments in Vaccines, edited by Voller et al., University Park Press, Baltimore, Md., U.S.A. 1978.

It is foreseen that compositions of the present invention will be used to formulate vaccines containing antigens derived from a wide variety of sources. For example, antigens may include human, bacterial, or viral nucleic acid, pathogen derived antigen or antigenic preparations, tumour derived antigen or antigenic preparations, host-derived antigens, including peptides derived from IgE, such as the histamine releasing decapeptide of IgE (known as the Stanworth decapeptide), recombinantly produced protein or peptides, and chimeric fusion proteins.

There is provided by the present invention a mucosal vaccine composition comprising an antigen, and a haemolytic saponin. Accordingly, there is provided a method of treatment of an individual susceptible to or suffering from a disease by the administration of a composition as substantially herein described to a mucosal surface of said individual.

Furthermore, there is described a method of inducing a systemic antigen specific immune response in a mammal, comprising administering to a mucosal surface of said mammal a composition comprising an antigen and a haemolytic saponin. Further there is provided a method of manufacture of a vaccine or adjuvant are also provided, comprising taking a saponin and taking a CpG molecule and admixing them with an antigen.

Examples of suitable pharmaceutically acceptable excipients for use in the combinations of the present invention include water, phosphate buffered saline, isotonic buffer solutions.

The present invention is illustrated by, but not restricted to, the following examples.

EXAMPLE 1

The use of QS21 and CpG for the Intranasal Boosting of Systemic Antibodies to Lipo-OspA In this example we investigated whether lytic saponins such as QS21 and immunostimulants such as CpG were able to enhance in a synergistic fashion systemic immunological responses to an intranasal boosting vaccination of mice. Female Balb/c mice (5 animals per group), aged 8 weeks, were immunized intramuscularly with lipo-OspA (1 μg) formulated onto alum (50 μg). After 3 months, the mice were boosted intranasally (under anesthesia) with 10 μl of solution (5 μl per nostril, delivered as droplets by pipette) containing 5 μg lipo-OspA in either A: PBS; B: 20 μg CpG 1001 (TCC ATG AGC TTC CTG ACG TT, Krieg 1826); C: 5 μg QS21 (obtained from Cambridge Biotech, USA); D: 20 μg CpG 1001±5 μg QS21; or, E: by intra muscular injection of 1 μg lipo-OspA adsorbed onto alum (50 μg). FIGS. 1 and 2 show the OspA specific IgG titres and LA2 titres 14 days after the nasal boosting.

Results

CpG as well as QS21 improve significantly the intranasal boosting of systemic antibodies to Lipo-OspA. Moreover, when both adjuvants are combined, a synergistic effect on those responses is clearly demonstrated, especially in term of LA2 antibodies. Humoral responses elicited in the presence of QS21 and CpG are significantly higher than those induced by the parenteral booster. Taken together, these results show clearly the potential of intranasal formulations combining a lytic saponin and an immunostimulant.

We claim:

1. An immunogenic composition comprising a saponin an immunostimulatory oligonucleotide comprising an unmethylated CG dinucleotide and a tumor-associated antigen.

2. An immunogenic composition as claimed in claim 1 wherein said saponin is QS21.

3. An immunogenic composition as claimed in claim 1 wherein said immunostimulatory oligonucleotide comprises a sequence of XXCGYY, wherein X is a purine and Y is a pyrimidine.

4. An immunogenic composition as claimed in claim 1 wherein said immunostimulatory oligonucleotide is selected from the group comprising: TCC ATG ACG TTC CTG ACG TT (SEQ ID NO:1); TCT CCC AGC GTG CGC CAT (SEQ ID NO:2); ACC GAT GAC GTC GCC GGT GAC GGC ACC ACG (SEQ ID NO:3).

5. A method of treatment of an individual susceptible to or suffering from a disease by the administration to an individual an immunogenic composition as claimed in any of claims 1 to 4.

* * * * *

SEQUENCE LISTING

```
<160> NUMBER OF SEQ ID NOS:  3

<210> SEQ ID NO 1
<211> LENGTH: 20
<212> TYPE: DNA
<213> ORGANISM: Artifical Sequence
<220> FEATURE:
<223> OTHER INFORMATION: Immunostimulatory oligonucleotide sequence
      comprising
<223> OTHER INFORMATION: one or more CpG motifs

<400> SEQUENCE: 1
tccatgacgt tcctgacgtt                                                   20

<210> SEQ ID NO 2
<211> LENGTH: 18
<212> TYPE: DNA
<213> ORGANISM: Artificial Sequence
<220> FEATURE:
<223> OTHER INFORMATION: Immunostimulatory oligonucleotide sequence
      comprising
<223> OTHER INFORMATION: one or more CpG motifs

<400> SEQUENCE: 2
tctcccagcg tgcgccat                                                     18

<210> SEQ ID NO 3
<211> LENGTH: 30
<212> TYPE: DNA
<213> ORGANISM: Artificial Sequence
<220> FEATURE:
<223> OTHER INFORMATION: Immunostimulatory oligonucleotide sequence
      comprising
<223> OTHER INFORMATION: one or more CpG motifs

<400> SEQUENCE: 3
accgatgacg tcgccggtga cggcaccacg                                        30
```